United States Patent
Liu et al.

(10) Patent No.: US 11,481,937 B2
(45) Date of Patent: Oct. 25, 2022

(54) POSITRON EMISSION TOMOGRAPHY IMAGE RECONSTRUCTION METHOD

(71) Applicant: Zhejiang University, Hangzhou (CN)

(72) Inventors: Huafeng Liu, Hangzhou (CN); Bo Wang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 86 days.

(21) Appl. No.: 17/060,008

(22) Filed: Sep. 30, 2020

(65) Prior Publication Data
US 2021/0366169 A1    Nov. 25, 2021

Related U.S. Application Data

(63) Continuation-in-part of application No. PCT/CN2020/117949, filed on Sep. 25, 2020.

(30) Foreign Application Priority Data

May 21, 2020 (CN) .......................... 202010436333.4

(51) Int. Cl.
*G06T 7/00* (2017.01)
*G06T 11/00* (2006.01)
(Continued)

(52) U.S. Cl.
CPC .......... *G06T 11/008* (2013.01); *A61B 6/037* (2013.01); *A61B 6/4241* (2013.01); *G06N 3/04* (2013.01);
(Continued)

(58) Field of Classification Search
CPC ..... G06T 11/008; G06T 5/002; G06T 7/0012; G06T 11/006; G06T 2207/10104;
(Continued)

(56) References Cited

U.S. PATENT DOCUMENTS

2020/0311878 A1* 10/2020 Matsuura ............... G06V 10/82

OTHER PUBLICATIONS

Cui, Jianan, et al. "Structure and tracer kinetics-driven dynamic PET reconstruction." IEEE Transactions on Radiation and Plasma Medical Sciences 4.4 (2019): 400-409. (Year: 2019).*

(Continued)

*Primary Examiner* — Sean M Conner
*Assistant Examiner* — Denise G Alfonso
(74) *Attorney, Agent, or Firm* — Matthias Scholl P.C.; Matthias Scholl

(57) ABSTRACT

A PET image reconstruction method, including: 1) injecting a PET radioactive tracer into a biological tissue, scanning by a PET device, and detecting and counting coincidence photons to obtain an original protection data matrix; 2) establishing a measurement equation model; 3) splitting the reconstruction problem into a first sub-problem and a second sub-problem; 4) solving the first sub-problem by a filtered back-projection layer, solving the second sub-problem by an improved denoising convolutional neural network, where the filtered back-projection layer and the improved denoising convolutional neural network are connected in series to form a filtered back-projection network (FBP-Net); 5) inputting original projection data into the FBP-Net, and using an image as a tag to adjust parameters of the FBP-Net to reduce an error between an output of the FBP-Net and the tag; and 6) inputting projection data to be reconstructed into the trained FBP-Net to obtain a desired reconstructed image.

8 Claims, 3 Drawing Sheets

(51) Int. Cl.
 *G06T 5/00* (2006.01)
 *G06N 3/04* (2006.01)
 *G06N 3/08* (2006.01)
 *A61B 6/00* (2006.01)
 *A61B 6/03* (2006.01)

(52) U.S. Cl.
 CPC .............. *G06N 3/084* (2013.01); *G06T 5/002* (2013.01); *G06T 7/0012* (2013.01); *G06T 11/006* (2013.01); *G06T 2207/10104* (2013.01); *G06T 2207/20081* (2013.01); *G06T 2207/20084* (2013.01); *G06T 2207/30004* (2013.01)

(58) Field of Classification Search
 CPC . G06T 2207/20081; G06T 2207/20084; G06T 2207/30004; G06T 11/003; A61B 6/4241; A61B 6/5205; G06N 3/04; G06N 3/084
 See application file for complete search history.

(56) References Cited

OTHER PUBLICATIONS

Syben, Christopher, et al. "Precision learning: reconstruction filter kernel discretization." arXiv preprint arXiv:1710.06287 (2017). (Year: 2017).*

He, Ji, Yongbo Wang, and Jianhua Ma. "Radon inversion via deep learning." IEEE Transactions on Medical Imaging 39.6 (2020): 2076-2087. (Year: 2020).*

Jayalakshmi, T., and A. Santhakumaran. "Statistical normalization and back propagation for classification." International Journal of Computer Theory and Engineering 3.1 (2011): 1793-8201. (Year: 2011).*

* cited by examiner

POSITRON EMISSION TOMOGRAPHY IMAGE RECONSTRUCTION METHOD

CROSS-REFERENCE TO RELAYED APPLICATIONS

This application is a continuation-in-part of International Patent Application No. PCT/CN2020/117949 with an international filing date of Sep. 25, 2020, designating the United States, now pending, and further claims foreign priority benefits to Chinese Patent Application No. 202010436333.4 filed May 21, 2020. The contents of all of the aforementioned applications, including any intervening amendments thereto, are incorporated herein by reference. Inquiries from the public to applicants or assignees concerning this document or the related applications should be directed to: Matthias Scholl P.C., Attn. Dr. Matthias Scholl Esq., 245 First Street, 18th Floor, Cambridge, Mass. 02142.

BACKGROUND

The disclosure relates to the field of biomedical image analysis, and more particularly to a positron emission tomography (PET) image reconstruction method involving a filtered back-projection algorithm and a neural network.

Positron emission tomography (PET) is an imaging technique that uses radioactive substances to visualize and measure metabolic processes in the body. PET is mainly used in the area of medical imaging for detecting or measuring changes in physiological activities like metabolism, blood flow, regional chemical composition, and absorption, and therefore, also called a functional imaging technique. However, disadvantages including low resolution, low counting rate, and noise are associated with the PET imaging.

To acquire high-quality PET images, PET reconstruction algorithms such as analytical reconstruction algorithms, iterative reconstruction algorithms and deep learning reconstruction methods are used. In the analytical reconstruction algorithms such as filtered back-projection (FBP) algorithms, frequency-domain filtering is performed on the sinogram on the basis of the central slice theorem, and back projection is then performed. The reconstructed images obtained by such methods contain much noise and wheel-like artifacts. The iterative reconstruction algorithms use a Poisson or Gaussian mode to describe noise and establish a reconstructed target function. To suppress noise in a reconstructed image, priori constraints such as Markov random fields or TV are often added in the target function. There is a wide variety of priori forms, so it is difficult to determine which priori form is optimal. Compared with the analytical reconstruction algorithms, the iterative reconstruction algorithms suppress noise in the reconstructed image by using a noise model. However, the iterative reconstruction algorithms have a large amount of computation and slow speed, and the priori forms and hyper-parameters are selected by experience, without uniform standards.

In recent years, deep neural networks have been used to reconstruct PET images. The relatively mature deep neural network structures such as U-net, generative adversarial networks (GANs) or encoding-decoding structures are used to input, into a neural network, sinograms or low-quality reconstructed images obtained by a conventional method, and high-quality reconstructed images are output by supervised learning by the neural network. Although these methods have made some achievements in reconstruction, the networks used by these methods look like black boxes and are difficult to interpret. In addition, to achieve better results, these methods are often trained by a large amount of high-quality data which is scarce in the field of medical images.

SUMMARY

The disclosure provides a PET image reconstruction method involving a filtered back-projection algorithm and a neural network. The method comprises image reconstruction and denoising, which are achieved respectively by a filtered back-projection layer and an improved denoising convolutional neural network.

The PET image reconstruction method comprises:

1) injecting a PET radioactive tracer into a biological tissue, scanning by a PET device, and detecting and counting coincidence photons to obtain an original protection data matrix Y;

2) establishing a measurement equation model according to a PET imaging principle:

$$Y=GX+R+S \quad (1);$$

where G is a system matrix, X is a real concentration distribution map of the radioactive tracer, R is a number of random photons during the measurement process, and S is a number of scattered photons during the measurement process;

3) splitting the reconstruction problem into a first sub-problem and a second sub-problem, $$X=F_1(Y)-F_2(R+S) \quad (2);$$

where the first sub-problem is to reconstruct the original projection data matrix Y to obtain a preliminarily reconstructed image $F_1(Y)$ containing noise; and the second sub-problem is to remove a noise $F_2(R+S)$ in the $F_1(Y)$ to a PET reconstructed image X;

4) solving the first sub-problem by a filtered back-projection (FBP) layer, solving the second sub-problem by an improved denoising convolutional neural network (DnCNN), where the filtered back-projection layer and the improved denoising convolutional neural network are connected in series to form a filtered back-projection network (FBP-Net);

5) in a training stage, inputting original projection data (sinogram) into the FBP-Net, and using an image obtained by a conventional reconstruction algorithm as a tag to adjust parameters of the FBP-Net to reduce an error between an output of the FBP-Net and the tag; and 6) in an estimation stage, inputting projection data to be reconstructed into the trained FBP-Net to obtain a desired reconstructed image.

In a class of this embodiment, in 1), the scanning by a PET device is static scanning or dynamic scanning.

In a class of this embodiment, in 4), PET projection data is input to the filtered back-projection layer to yield the preliminarily reconstructed image containing noise.

In a class of this embodiment, the filtered back-projection layer operates based on a filtered back-projection algorithm comprising frequency-domain filtering and back projection; the back projection uses a conventional filtered back-projection algorithm, the frequency-domain filtering involves a learnable filter, and the projection data of each angle corresponds to an independent one-dimensional frequency-domain filter.

In a class of this embodiment, in 4), the improved denoising convolutional neural network removes the noise in the preliminarily reconstructed image by residual learning.

In a class of this embodiment, the improved denoising convolutional neural network comprises eight 2D convolutional layers and one normalization layer. Each convolutional layer comprises 64 3×3 filters, and the first seven convolutional layers use an activation function ReLU and batch normalization (BN). The eight 2D convolutional layers learn a residual error between the reconstructed image containing noise and a clean reconstructed image. The output of the eighth convolutional layer is subtracted from the input of the improved denoising convolutional neural network, and the result is then processed by the normalization layer to obtain a clean reconstructed image.

In a class of this embodiment, in 5), both the original projection data (sinogram) and the tag are subjected to single-frame normalization:

$$X_{norm} = \frac{X - X_{min}}{X_{max} - X_{min}}; \quad (3)$$

where $X_{min}$ and $X_{max}$ are minimum and maximum values of single-frame data, respectively.

In a class of this embodiment, in 5), the training stage comprises:

5.1) initializing parameters of the FBP-Net, initializing all frequency-domain filters of the FBP layer by a ramp filter, and initializing parameters in the improved DnCNN by a truncated normal distribution;

5.2) inputting sinogram in a training set into the FBP-Net, calculating an output of each layer by a forward propagation formula, and obtaining a final output of the FBP-Net;

5.3) calculating a loss function between the output of the FBP-Net and the tag:

$$\text{loss} = \frac{1}{N}\sum_{i=1}^{N}(\hat{X}(i) - X(i))^2; \quad (4)$$

where $\hat{X}(i)$ is an estimated value of an $i^{th}$ sample output by the FBP-Net, and $X(i)$ is a tag of the $i^{th}$ sample;

5.4) obtaining a partial derivative of the loss function, and updating learnable parameters in the FBP-Net by an Adam algorithm; and 5.5) repeating operations in 5.2) to 5.4) until a change in a numerical value of the loss value is less than $10^{-5}$ In a class of this embodiment, in 6), the projection data to be reconstructed is normalized before being input into the trained FBP-Net.

In a class of this embodiment, data input to the FBP-Net is 2D PET scanning data.

The following advantages are associated with the method of the disclosure. By combining a conventional filtered back-projection algorithm and a neural network, an interpretable deep neural network structure is provided for reconstruction of PET images. The reconstruction problem is split into two sub-problems, i.e., reconstruction and denoising, which are solved by a filtered back-projection layer and an improved denoising convolutional neural network, respectively. In the filtered back-projection layer, a frequency-domain filter is regarded as being learnable, and a reconstructed image containing noise is reconstructed from the sinogram; and, in the improved DnCNN, the noise in the reconstructed image is removed to obtain a clear reconstructed image. According to the disclosure, the problem that deep learning is difficult to interpret when being used for image reconstruction is solved, and a clear PET image can still be reconstructed in case of a low counting rate.

BRIEF DESCRIPTION OF THE DRAWINGS

FIG. 1A shows a training stage, and FIG. 1B shows a reconstruction stage;

DETAILED DESCRIPTION

To further illustrate, embodiments detailing a positron emission tomography (PET) image reconstruction method are described below. It should be noted that the following embodiments are intended to describe and not to limit the disclosure.

Figures 1A, 1B:
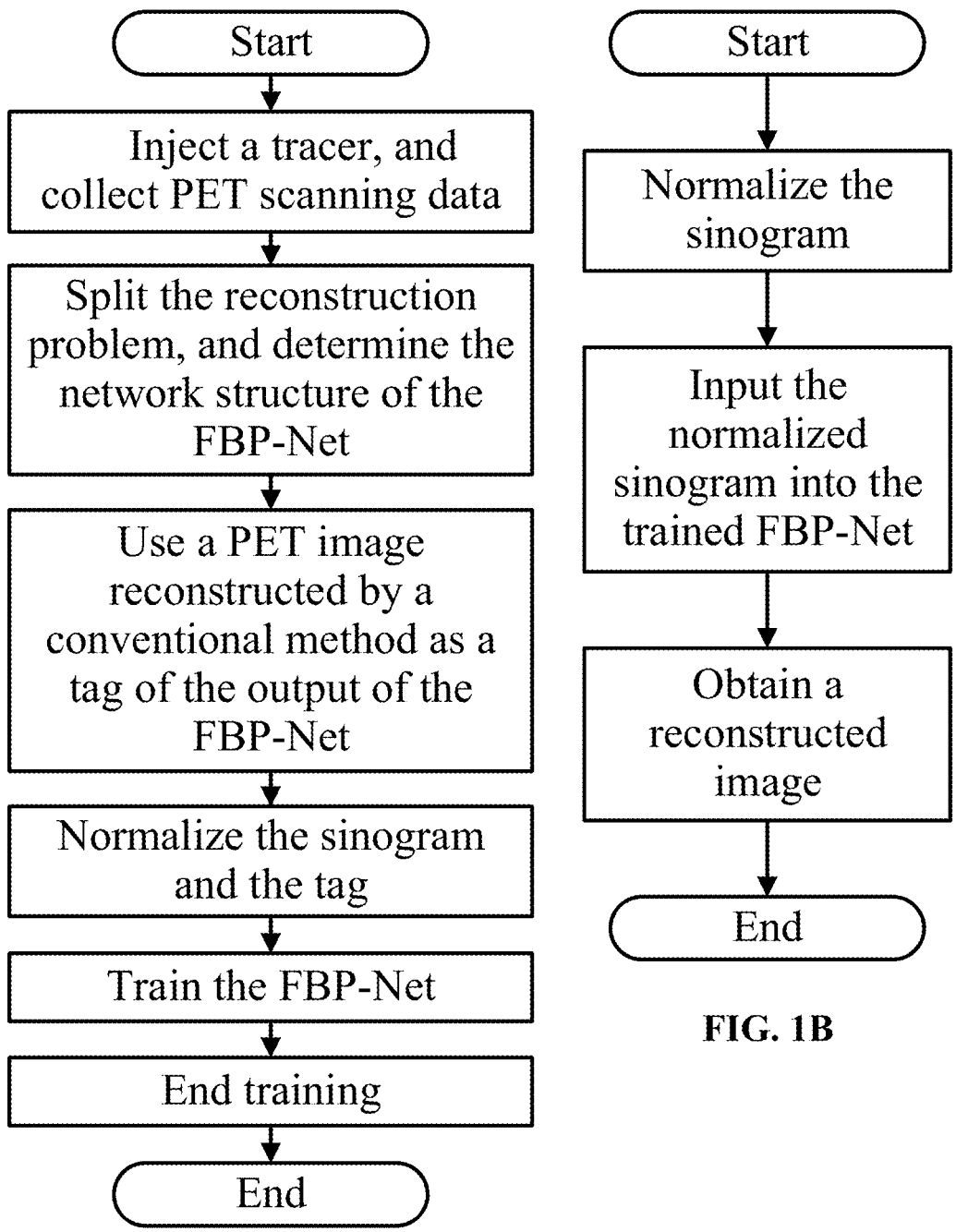
FIGS. 1A-1B are flowcharts of a positron emission tomography (PET) image reconstruction method according to one embodiment of the disclosure, where

The disclosure provides a PET image reconstruction method involving a filtered back-projection algorithm and a neural network. The flowchart of the method is shown in FIGS. 1A-1B. The PET image reconstruction method comprises the following steps.

1. Data collection: A proper amount of PET radioactive tracer is injected into a research object; the research object is statically or dynamically scanned by a PET device, and coincidence photons are detected and counted to obtain an original protection data matrix Y.

Figure 2:
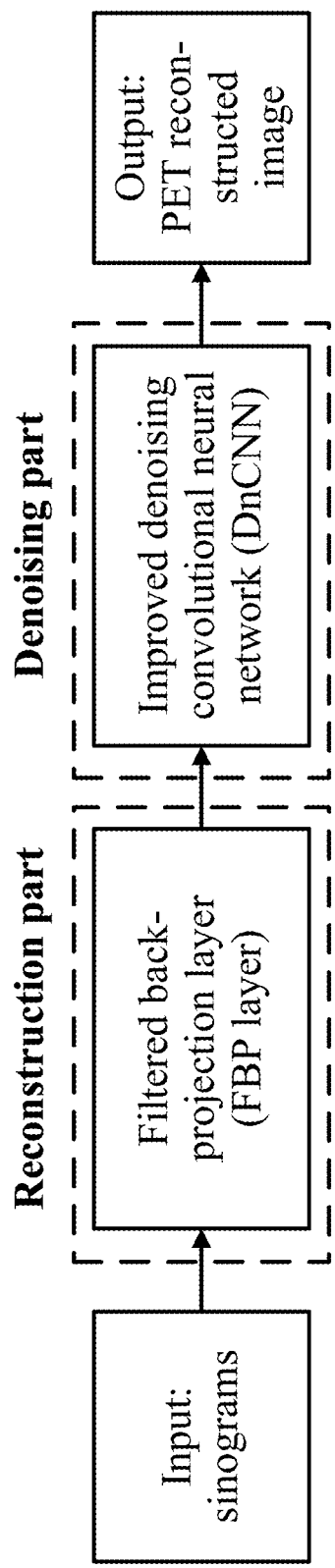
FIG. 2 is a structure diagram of an FBP-Net according to the disclosure.

2. The reconstruction problem is split, and the structure of the neural network is determined as shown in FIG. 2.

A measurement equation model is established according to a PET imaging principle:

$$Y = GX + R + S \quad (1);$$

where G is a system matrix, X is a real concentration distribution map of the tracer, R is the number of random photons during the measurement process, and S is the number of scattered photons during the measurement process.

The measurement equation model is transformed to split the reconstruction problem into a first sub-problem and a second sub-problem:

$$X = F_1(Y) - F_2(R+S) \quad (2).$$

The first sub-problem is to reconstruct the original projection data matrix Y to obtain a preliminarily reconstructed image $F_1(Y)$. The preliminarily reconstructed image $F_1(Y)$ contains a large amount of noise. Since the PET original detection data contains scattering coincidence events and random coincidence events, the number of true coincidence events available for reconstruction is less than half of the total number of detection events. If scattering correction and random correction are not carried out, a reconstructed image will be affected by random photons and scattered photons, and the image will not be good enough in contrast and detail. The noise here means that the random photons and scattered photons will lead to low quality of the reconstructed image when random correction and scattering correction are not carried out. The second sub-problem is to remove a noise the noise $F_2(R+S)$ in the $F_1(Y)$ to obtain a PET reconstructed image X. In the PET reconstructed image X, the influences of the scattered photons and random photons on the reconstructed image are eliminated, and possible artifacts in the preliminarily reconstructed image $F_1(Y)$ obtained in the previous step are eliminated to obtain a reconstructed image with high contrast, clear details and no artifacts. The PET reconstructed image X is a high-quality PET reconstructed image X.

The first sub-problem is solved by a filtered back-projection layer, and the second sub-problem is solved by an improved denoising convolutional neural network. The filtered back-projection layer and the improved denoising convolutional neural network are connected in series to form a filtered back-projection network, i.e., FBP-Net.

PET projection data is input to the filtered back-projection layer to yield the preliminarily reconstructed image containing noise. The filtered back-projection layer operates based on a filtered back-projection algorithm comprising frequency-domain filtering and back projection, where the back projection is the same as a conventional filtered back-projection algorithm, the frequency-domain filtering involves a learnable filter, and the projection data of each angle corresponds to an independent one-dimensional frequency-domain filter. The improved denoising convolutional neural network removes the noise in the preliminarily reconstructed image by residual learning. The improved denoising convolutional neural network comprises eight 2D convolutional layers and one normalization layer. Each convolutional layer comprises 64 3×3 filters, and the first seven convolutional layers use an activation function ReLU and batch normalization (BN). The eight 2D convolutional layers learn a residual error between the reconstructed image containing noise and a clean reconstructed image. The output of the eighth convolutional layer is subtracted from the input of the improved denoising convolutional neural network, and the result is then processed by the normalization layer to obtain a clean reconstructed image, i.e., a denoised PET reconstructed image.

(3) Training Stage

A sinogram is reconstructed by a conventional reconstruction algorithm to obtain an image as a tag, and both the sinogram and the tag are subjected to single-frame normalization. The normalization formula is:

$$X_{norm} = \frac{X - X_{min}}{X_{max} - X_{min}}; \quad (3)$$

where $X_{min}$ and $X_{max}$ are the minimum and maximum values of single-frame data, respectively. Parameters of the FBP-Net are initialized. The frequency-domain of the FBP layer is initialized by a ramp filter and the parameters in the improved DnCNN are initialized by a truncated normal distribution. A sinogram in a training set is input into the FBP-Net, the output of each layer is calculated by a forward propagation formula, and the final output of the FBP-Net is obtained. A loss function between the output of the FBP-Net and the tag is calculated:

$$loss = \frac{1}{N}\sum_{i=1}^{N}(\hat{X}(i) - X(i))^2; \quad (4)$$

where $\hat{X}(i)$ is the estimated value of the $i^{th}$ sample output by the FBP-Net, and $X(i)$ is the tag of the $i^{th}$ sample. A partial derivative of the loss function is obtained, and learnable parameters in the FBP-Net are updated by an Adam algorithm. Forward propagation and reverse derivation are repeated and the parameters of the FBP-Net are continuously updated until the change in the numerical value of the loss function is small enough and stable, that is, the error between the output of the FBP-Net and the tag is as small as possible. This is because the numerical value of the loss function (loss) drops rapidly at the beginning of training, but the numerical value of the loss drops very slowly and gradually becomes stable after a certain number of iterations. If the training is continuously performed at this time, the time cost will be increased, but a very small improvement will be obtained. Therefore, the training ends when the change in a numerical value of the loss function is small enough, that is, when the numerical value of the loss drops very slowly. In this embodiment, when the change in the numerical value of the loss function is less than $10^{-5}$, training is to be carried out.

(4) Estimation Stage

The sinogram to be reconstructed is normalized and then input into the trained FBP-Net to directly obtain a desired reconstructed image. In this reconstructed image, the influences of the scattered photons and random photons on the reconstructed image are eliminated, and possible artifacts in the preliminarily reconstructed image are eliminated. Therefore, this reconstructed image is a high-quality PET reconstructed image with high contrast, clear details and no artifacts.

The following experiment is conducted on the basis of Monte Carlo simulation data to verify the effectiveness of this embodiment. The experiment is conducted on a server with Ubuntu 18.04 LTS system, having a memory of 128 G, a deep learning framework of tensorow 1.13.1 and a graphics card of NVIDIA TITAN RTX 24 GB used for accelerating code operation.

The tracer for simulation is $^{18}$F-FDG, the body model is chest, and the scanner for simulation is Siemens Biograph PET/CT. The scanning time for simulation is 40 min, there are 18 time frames, three counting rates (i.e., $1\times10^5$, $5\times10^5$ and $1\times10^6$) are considered, and 30 sets of dynamic PET data are simulated for each counting rate. The simulated data of the three counting rates are randomly classified into a training set (1134 sinograms) and a test set (486 sinograms). The training set is used to learn the parameters of the FBP-Net, and the test set is used to verify the performance of the FBP-Net.

Figure 3:
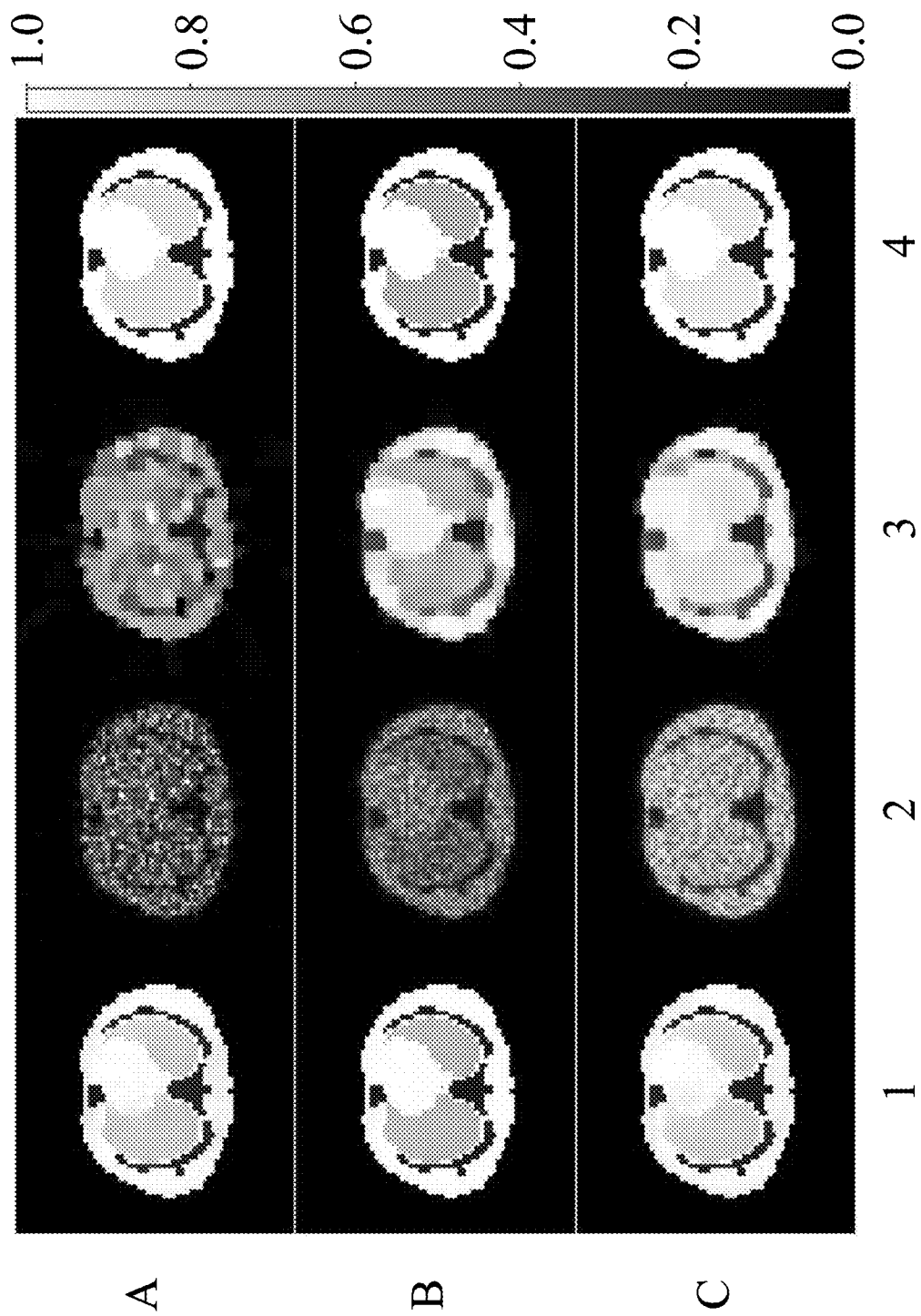
FIG. 3 is a comparison diagram of $^{18}$F-FDG reconstructed images by different methods at different counting rates, where the images in the first column are reconstructed images obtained by the disclosure, the images in the second column are reconstructed images obtained by an MLEM algorithm, the images in the third column are reconstructed images obtained by a TV algorithm, the images in the fourth column are true values, and the counting rates corresponding to the rows A, B and C are $1\times10^5$, $5\times10^5$ and $1\times10^6$, respectively.

In FIG. 3, the reconstructed images obtained by the disclosure and conventional reconstruction methods at three counting rates are compared. The images in the first column are reconstructed images obtained by the disclosure, the images in the second column are reconstructed images obtained by an MLEM algorithm, the images in the third column are reconstructed images obtained by a TV algorithm, the images in the fourth column are true values, and the counting rates corresponding to the rows A, B and C are $1\times10^5$, $5\times10^5$ and $1\times10^6$, respectively. The reconstruction images obtained by the disclosure have rich details and low noise, and are closest to the true value images; the reconstructed images obtained by the MLEM algorithm contain a large amount of noise; and, the reconstructed images obtained by the TV algorithm are too smooth, and some details are lost. When the counting rate changes from high to low, the reconstructed images obtained by the disclosure are almost unaffected and are still closest to the true value images; in the reconstructed images obtained by the MLEM algorithm, the noise is higher and higher; and, in the reconstructed images obtained by the TV algorithm, more and more details are lost, or even non-uniform patches appear. It can be found that, the method provided by the disclosure can obtain high-quality PET reconstructed images, and is insensitive to the counting rate and can still reconstruct high-quality images even in case of a low counting rate.

In this embodiment, the input of the FBP-Net is 2D PET scanning data. If the original collected data is in form of 3D, the data needs to be converted into 2D scanning data by a method such as SSRB or FORB.

In the disclosure, by combining a conventional filtered back-projection algorithm and a neural network, an interpretable deep neural network structure is proposed for reconstruction of PET images. The reconstruction problem is split into two sub-problems, i.e., reconstruction and denoising, which are solved by a filtered back-projection layer and an improved denoising convolutional neural network, respectively. In the filtered back-projection layer, a frequency-domain filter is regarded as being learnable, and a reconstructed image containing noise is reconstructed from sinograms; and, in the improved DnCNN, the noise in the reconstructed image is removed to obtain a clear reconstructed image. According to the disclosure, the problem that deep learning is difficult to interpret when being used for image reconstruction is solved, and a clear PET image can still be reconstructed in case of a low counting rate.

It will be obvious to those skilled in the art that changes and modifications may be made, and therefore, the aim in the appended claims is to cover all such changes and modifications.

What is claimed is:

1. A method, comprising:
   1) injecting a positron emission tomography (PET) radioactive tracer into a biological tissue, scanning by a PET device, and detecting and counting coincidence photons to obtain an original protection data matrix Y;
   2) establishing a measurement equation model according to a PET imaging principle:

$$Y=GX+R+S \quad (1);$$

wherein G is a system matrix, X is a real concentration distribution map of the radioactive tracer, R is a number of random photons during a measurement process, and S is a number of scattered photons during the measurement process;
   3) Splitting a reconstruction problem into a first sub-problem and a second sub-problem, $$X=F_1(Y)-F_2(R+S) \quad (2);$$

wherein the first sub-problem is to reconstruct the original projection data matrix Y to obtain a preliminarily reconstructed image $F_1(Y)$ containing noise; and the second sub-problem is to remove a noise $F_2$ (R+S) in the preliminarily reconstructed image $F_1(Y)$ to a PET reconstructed image X;
   4) solving the first sub-problem by a filtered back-projection (FBP) layer, and solving the second sub-problem by an improved denoising convolutional neural network (DnCNN), wherein the filtered back-projection layer and the improved denoising convolutional neural network are connected in series to form a filtered back-projection network (FBP-Net);
   5) in a training stage, inputting original projection data into the FBP-Net, and using an image obtained by a conventional reconstruction algorithm as a tag to adjust parameters of the FBP-Net to reduce an error between an output of the FBP-Net and the tag; and
   6) in an estimation stage, inputting projection data to be reconstructed into the trained FBP-Net to obtain a desired reconstructed image;

wherein:
   in 5), the training stage comprises:
   5.1) initializing parameters of the FBP-Net, initializing all frequency-domain filters of the FBP layer by a ramp filter, and initializing parameters in the improved DnCNN by a truncated normal distribution;
   5.2) inputting sinogram in a training set into the FBP-Net, calculating an output of each layer by a forward propagation formula, and obtaining a final output of the FBP-Net;
   5.3) calculating a loss function between the output of the FBP-Net and the tag:

$$\text{loss} = \frac{1}{N}\sum_{i=1}^{N}(\hat{X}(i) - X(i))^2; \quad (4)$$

wherein $\hat{X}(i)$ is an estimated value of an $i^{th}$ sample output by the FBP-Net, and X(i) is a tag of the $i^{th}$ sample;
   5.4) obtaining a partial derivative of the loss function, and updating learnable parameters in the FBP-Net by an Adam algorithm; and
   5.5) repeating operations in 5.2) to 5.4) until a change in a numerical value of the loss value is less than $10^{-5}$.

2. The method of claim 1, wherein in 4), PET projection data is input to the filtered back-projection layer to yield the preliminarily reconstructed image containing noise.

3. The method of claim 2, wherein the filtered back-projection layer operates based on a filtered back-projection algorithm comprising frequency-domain filtering and back projection; the back projection uses a conventional filtered back-projection algorithm, the frequency-domain filtering involves a learnable filter, and the projection data of each angle corresponds to an independent one-dimensional frequency-domain filter.

4. The method of claim 1, wherein in 4), the improved denoising convolutional neural network removes the noise in the preliminarily reconstructed image by residual learning.

5. The method of claim 4, wherein the improved denoising convolutional neural network comprises eight 2D convolutional layers and one normalization layer; each convolutional layer comprises 64 3×3 filters, and first seven convolutional layers use an activation function ReLU and batch normalization (BN); the eight 2D convolutional layers learn a residual error between the reconstructed image containing noise and a clean reconstructed image; an output of an eighth convolutional layer is subtracted from an input of the improved denoising convolutional neural network, and a result is then processed by the one normalization layer to obtain a clean reconstructed image.

6. The method of claim 1, wherein in 5), both the original projection data and the tag are subjected to single-frame normalization:

$$X_{norm} = \frac{X - X_{min}}{X_{max} - X_{min}}; \quad (3)$$

wherein $X_{min}$ and $X_{max}$ are a minimum value and a maximum value of single-frame data, respectively.

7. The method of claim 1, wherein in 6), the projection data to be reconstructed is normalized before being input into the trained FBP-Net.

8. The method of claim 1, wherein data input to the FBP-Net is 2D PET scanning data.

* * * * *